US010251724B2

(12) United States Patent
McLachlin et al.

(10) Patent No.: US 10,251,724 B2
(45) Date of Patent: Apr. 9, 2019

(54) VERTEBRAL REFERENCE CLAMP

(71) Applicants: Stewart David McLachlin, Toronto (CA); Gal Sela, Toronto (CA); Kamyar Abhari, Toronto (CA); Kai Michael Hynna, Toronto (CA)

(72) Inventors: Stewart David McLachlin, Toronto (CA); Gal Sela, Toronto (CA); Kamyar Abhari, Toronto (CA); Kai Michael Hynna, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/584,132

(22) Filed: May 2, 2017

(65) Prior Publication Data
US 2018/0318035 A1 Nov. 8, 2018

(51) Int. Cl.
*A61B 34/00* (2016.01)
*A61B 90/00* (2016.01)
*A61B 34/20* (2016.01)
*A61B 90/96* (2016.01)
*A61B 17/70* (2006.01)
*A61B 17/00* (2006.01)

(52) U.S. Cl.
CPC .......... *A61B 90/39* (2016.02); *A61B 17/7074* (2013.01); *A61B 34/20* (2016.02); *A61B 90/96* (2016.02); *A61B 2017/00004* (2013.01); *A61B 2017/00938* (2013.01); *A61B 2034/2055* (2016.02); *A61B 2034/2072* (2016.02); *A61B 2090/3916* (2016.02); *A61B 2090/3937* (2016.02); *A61B 2090/3954* (2016.02); *A61B 2090/3966* (2016.02); *A61B 2090/3983* (2016.02); *A61B 2090/3991* (2016.02)

(58) Field of Classification Search
CPC ......... A61B 90/39; A61B 90/36; A61B 34/20; A61B 17/7074; A61B 2034/2055; A61B 2034/2072; A61B 2090/3916; A61B 2090/3937; A61B 2090/3954; A61B 2090/3966; A61B 2090/3983; A61B 2090/3991; A61B 2017/00004; A61B 2017/00938
USPC .......... 606/86 A, 130, 1; 600/407, 424, 414, 600/426, 411; 382/128, 276
See application file for complete search history.

(56) References Cited

U.S. PATENT DOCUMENTS 8,644,570 B2 * 2/2014 Hartmann ............ A61B 6/4405 382/128
9,839,450 B2 * 12/2017 Blain ...................... A61B 17/82
9,901,409 B2 * 2/2018 Yang ...................... A61B 5/055
(Continued)

*Primary Examiner* — Pedro Philogene
(74) *Attorney, Agent, or Firm* — Rowand LLP

(57) ABSTRACT

A reference tie to be secured around a portion of a spine during a surgical procedure and to be tracked by a surgical navigation system is described. The reference tie includes an elongate strap having a first strap end and a second strap end. The reference tie also includes a fastener joined to the elongate strap at the first strap end, the fastener for securing the first strap end to a portion of the second strap end. The elongate strap is configured to form a secured loop around the portion of the spine. The reference tie also includes a fiducial marker joined to at least one of the elongate strap or the fastener. The fiducial marker is trackable by the surgical navigation system.

18 Claims, 9 Drawing Sheets

(56) References Cited

U.S. PATENT DOCUMENTS

| | | | |
|---|---|---|---|
| 2006/0271055 A1* | 11/2006 | Thramann | A61B 17/7053 606/74 |
| 2009/0105766 A1* | 4/2009 | Thompson | A61B 17/7002 606/279 |
| 2015/0209119 A1 | 7/2015 | Theodore et al. | |
| 2016/0166335 A1 | 6/2016 | Roger et al. | |
| 2016/0317243 A1* | 11/2016 | Garcia Coni | A61G 13/121 |

* cited by examiner

VERTEBRAL REFERENCE CLAMP

FIELD

The present application generally relates to surgical navigation systems, and, in particular, to reference ties for conducting image-guided medical procedures.

BACKGROUND

In the field of medicine, medical professionals have traditionally relied on their past experience, intuition, or what they can see and feel to guide their decisions during a medical procedure. For example, when a medical professional is performing a surgical procedure using his or her eyes, the medical professional is guided by the eyes and other senses. Advanced imaging technology is now being included in surgical navigation systems for tracking objects during a surgical procedure. Surgical navigation systems rely on reference objects affixed to a portion of a patient's body. For example, surgical navigation systems may track surgical instruments relative to a reference object affixed to a patient. Alternatively, a movable portion of a patient may be tracked relative to a reference object affixed to a portion of a patient's body. Reference objects establish a frame of reference for tracking tools, instruments, or portions of a patient's anatomy during a medical procedure.

BRIEF SUMMARY

In one aspect, the present application describes a reference tie to be secured around a portion of a spine during a surgical procedure and to be tracked by a surgical navigation system. The reference tie includes an elongate strap having a first strap end and a second strap end. The reference tie also includes a fastener joined to the elongate strap at the first strap end. The fastener is for securing the first strap end to a portion of the second strap end. The elongate strap is configured to form a secured loop around the portion of the spine. The reference tie also includes a fiducial marker joined to at least one of the elongate strap or the fastener. The fiducial marker is trackable by the surgical navigation system.

In another aspect, the present application describes a reference tie to be secured to a portion of a spine during a surgical procedure and to be tracked by a surgical navigation system. The reference tie includes an attachment body having a plurality of attachment portions. The reference tie also includes at least one fastener joined to at least one of the plurality of attachment portions. At least one fastener is for securing one of the plurality of attachment portions to another of the plurality of attachment portions. The reference tie also includes a fiducial marker joined to at least one of the attachment body, the plurality of attachment portions, or the at least one fastener. The fiducial marker is trackable by the surgical navigation system.

Other aspects and features of the present application will be understood by those of ordinary skill in the art from a review of the following description of examples in conjunction with the accompanying figures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

BRIEF DESCRIPTION OF THE DRAWINGS

Reference will now be made, by way of example, to the accompanying drawings which show example embodiments of the present application.

Similar reference numerals may have been used in different figures to denote similar components.

DESCRIPTION OF EXAMPLE EMBODIMENTS

In the field of medicine, imaging and image guidance are components of clinical care. For example, optical tracking systems used during a medical procedure may track the position of a patient or surgical instruments that are within a field of view of an optical tracking camera. Three-dimensional sensor systems are increasingly being used in a wide variety of medical applications. Tracking of instruments relative to the patient and associated imaging data is often achieved by way of external hardware systems. Surgical navigation systems may register reference devices or markers to a patient, may register the patient to preoperative images, and may allow tracked instruments to be viewed on a visual display in the context of preoperative images.

Figure 1:
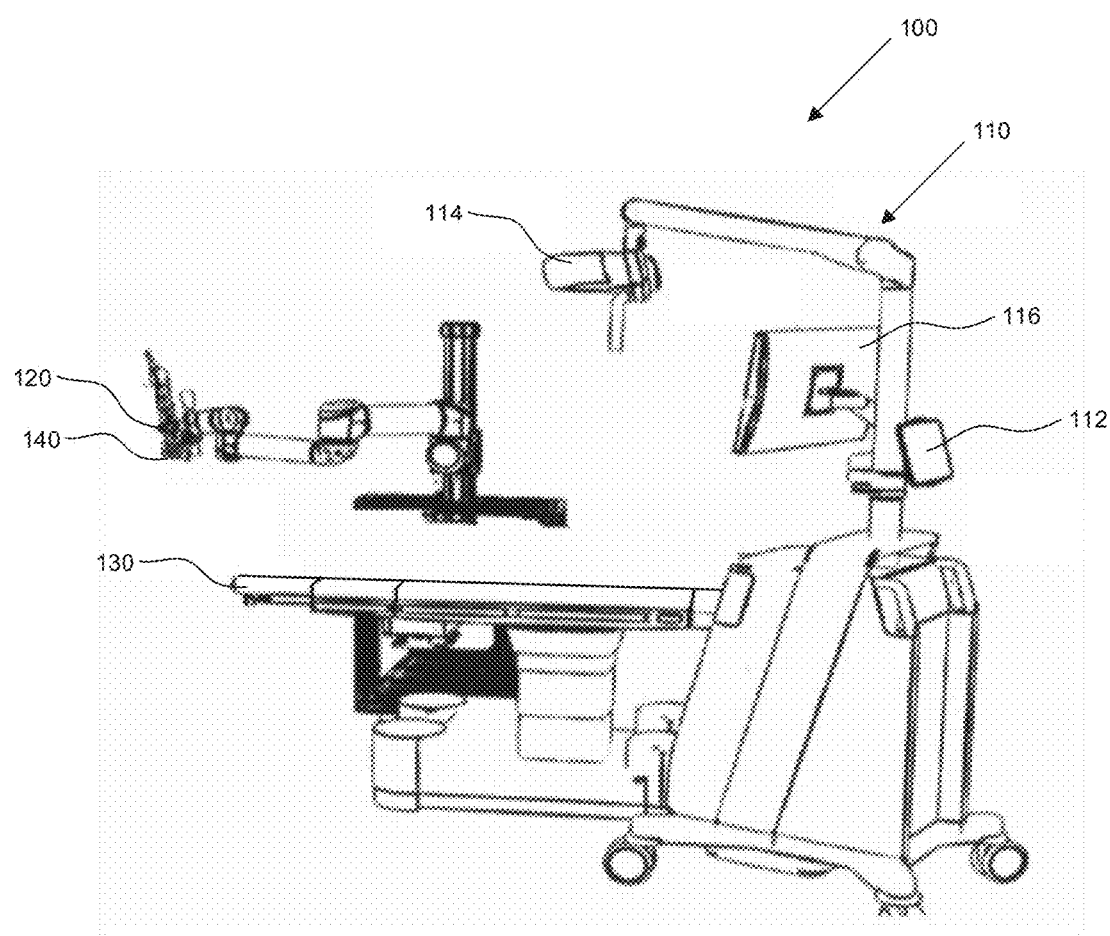
FIG. 1 is a diagram illustrating components of an exemplary surgical system.

Reference is now made to FIG. 1, which is a diagram illustrating components of an exemplary surgical system 100. FIG. 1 illustrates a surgical navigation system 110 including an equipment tower 112, an optical tracking camera 114, and a display unit 116.

The optical tracking camera 114 may include one or more camera lenses. Each camera lens may include a digital image sensor. In some embodiments, the optical tracking camera 114 may include two or more cameras oriented in a common direction. In some embodiments, the optical tracking camera 114 may be a stereoscopic camera and may be configured to capture images for generating three-dimensional images. The display unit 116 may be a video display positioned to be viewable by medical professionals responsible for a medical procedure. The surgical system 100 may also include a scope instrument 120 and a surgical platform 130.

In some embodiments, the scope instrument 120 may be an instrument to provide a surgeon with an enlarged view of portions of a patient. For example, the scope instrument 120 may be a microscope. In some embodiments, the scope instrument 120 may also be used to position or fixate other instruments near a patient during a surgical procedure. For example, the scope instrument 120 may include a lighting device for providing focused light rays to a portion of the patient's anatomy. In other examples, the scope instrument 120 may be a rigid frame or moveable arm for positioning surgical instruments during a procedure. In some embodiments, the surgical platform 130 may be a surgical table for positioning a patient during a surgical procedure.

In some embodiments, one or more reference ties may be secured to a patient positioned on the surgical platform 130. In some embodiments, one or more reference ties may be secured to the scope instrument 120 or other surgical instruments used during a surgical procedure. Reference ties may be detectable by components of surgical navigation systems. When reference ties are secured to objects within a surgical environment or to portions of a patient's anatomy, the reference ties may provide fixed points of reference or may provide information to a surgical navigation system. As will be described in the description that follows, in some embodiments, a reference tie may be a band, such as a strip of material to wrap around an object.

As will be described herein, a reference tie 140 may include a fiducial marker detectable by the optical tracking camera 114. The surgical navigation system 110 may register and/or track the position and movement of the reference tie 140. For example, the reference tie 140 may be affixed to the scope instrument 120 and the scope instrument 120 may be movable during a surgical procedure. It may be desirable to track movement of the scope instrument 120. For example, in one scenario, it may be desirable for the surgical navigation system 110 to detect movement of the scope instrument 120 and, subsequently, provide an alert to the medial team performing the medical procedure. That is, when the medical team requires the scope instrument 120 to be positioned in a specific location crucial to the medical procedure, the medical team may need to react if the scope instrument 120 changes position. In some embodiments, a real-time position of the scope instrument 120 may be displayed on the display unit 116.

In some embodiments, the surgical navigation system 110 may register objects having the reference tie 140 attached thereto. The surgical navigation system 110 may register the objects to an optical coordinate space and may determine position coordinates of a reference tie 140 in the optical coordinate space. The determined position coordinates may be coordinates within a defined surgical space relative to a set of axes. For example, a defined surgical space may be defined by an origin point (0, 0, 0), and position coordinates may be defined relative to the origin point. In some embodiments, the surgical space may include a three-dimensional space that a medical professional can define. The surgical space may be defined for a limited volume of space within the confines of the surgical navigation system 110 or the surgical space may be defined for a surgical operating room, where the surgical navigation system 110 is located.

For example, each of several objects in a surgical space may have a reference tie secured thereto. The surgical navigation system 110 may register each of the several objects in the surgical space using touch point registration. When conducting touch point registration, the surgical navigation system 110 may rely on a registration instrument having fiducial markers arranged in a unique geometric configuration attached thereon. The optical tracking camera 114 may recognize the fiducial markers of the registration instrument and track the location of the fiducial markers in the optical coordinate space. During touch point registration, the surgeon may utilize the registration instrument and successively touch each of the reference ties attached to the objects. When the registration instrument touches a reference tie, the surgical navigation system 110 may recognize the position of the reference tie based on the location of the registration instrument and map the reference tie to a coordinate position. Upon completion of the touch point registration, each of the several objects in the surgical space may be mapped to a coordinate position in the optical coordinate space and may serve as a reference point in the surgical space.

In a further example, the surgical navigation system 110 may be used to guide medical professionals to surgical areas of interest which may be occluded by anatomical tissue. For example, a surgeon may need to access a portion of a patient's spine adjacent the spinal cord. In some cases, open surgery may be more harmful than helpful in treating the patient. Thus, minimally invasive approaches may be preferred. However, minimally invasive surgical procedures could require that a surgeon navigate or operate on the patient's anatomy without having a direct view of the patient's anatomy that may be hidden from view. In some examples, a surgeon may assess a surgical area of interest using three-dimensional volumetric images of a patient (e.g., magnetic resonance imaging (MRI) or computerized tomography (CT)), and then choose the most optimal method for accessing the surgical area of interest. However, a surgeon may still be unable to traverse tissue while having clear view of the patient's anatomy. Accordingly, without the surgical navigation system 110, a surgeon may have no choice but to navigate surgical instruments "blind" relative to a patient, analogous to navigating a road with a trail map that indicates how far one should travel before changing course.

Some surgical navigation systems for spinal procedures, for example, may utilize a single reference marker or apparatus to represent the position of multiple vertebrae on a patient's spine. As an example, reference is made to FIG. 2, which illustrates a reference clamp 200 commonly used during a spinal procedure. The reference clamp 200 may include a set of fiducial markers 210. For example, the set of fiducial markers 210 may be arranged on a marker frame 212 in a unique pattern or geometry. In the example illustrated in FIG. 2, the set of fiducial markers 210 are arranged in a generally rectangular pattern. For example, a fiducial marker may be positioned at each corner of the generally rectangular pattern. Further, the marker frame 212 may be coupled to a clamp arm 220. The clamp arm 220 may be coupled to an attachment clamp 230. In some examples, the attachment clamp 230 may be a spring loaded clip for affixing the reference clamp 200 to a portion of a vertebra 240 on a spine.

Figure 2:
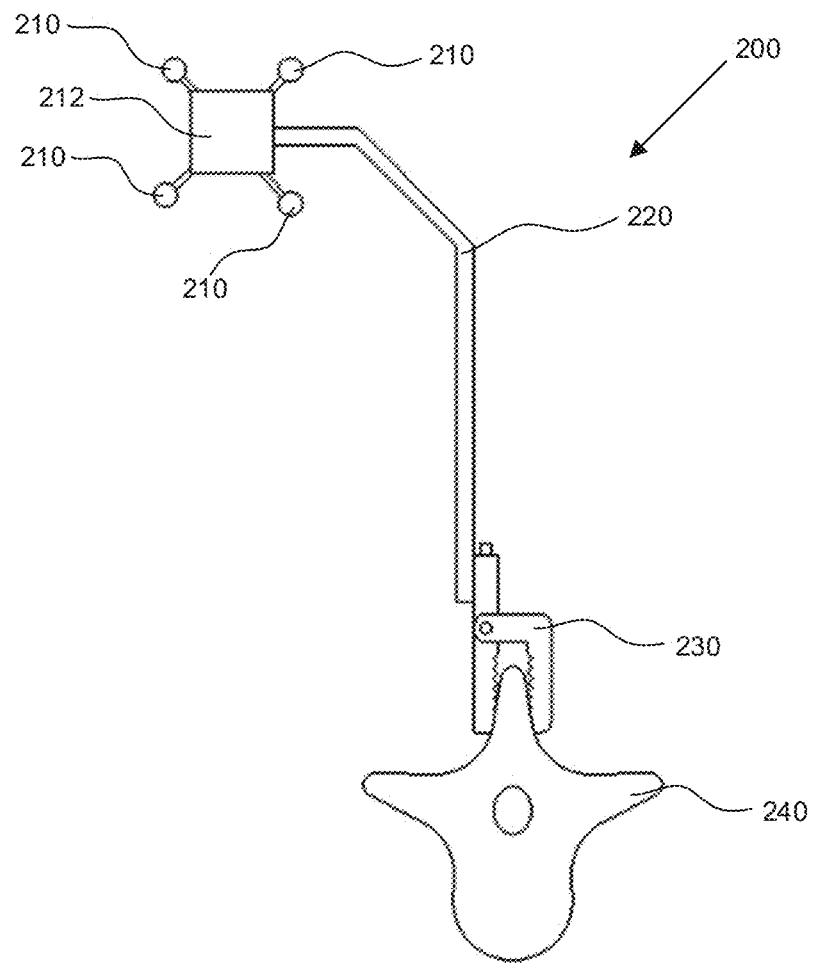
FIG. 2 is a common reference clamp providing a reference for multiple vertebra on a spine.

As illustrated in FIG. 2, the set of fiducial markers 210 may be collectively arranged at a position extended from the vertebra on the spine. The marker frame 212 is suspended by the clamp arm 220 in a position extending from the vertebra 240 and away from a patient's body. In the illustrated setup of FIG. 2, the reference clamp 200 may be the sole reference or "landmark" acting as a reference point for multiple vertebra on the spine.

Further, if local vertebra tracking for individual vertebra on a spine is desired, meticulous dissection of tissue or other anatomical features on multiple regions of the spine may be necessary to accommodate the attachment clamp 230. Meticulous dissection of tissue to provide sufficient clearance for affixing the attachment clamp 230 to a vertebra may be invasive to the patient's spine or to the area adjacent the patient's spine. In addition, fixating an attachment clamp 230 to vertebra bone may be challenging in cases where bone degeneration or other bone deformities are present. In cases where the vertebra bone is irregular in shape, it may be challenging for a surgeon to secure the attachment clamp 230 to the vertebra bone in a stable fashion.

To address some of the deficiencies of the example reference clamp 200 illustrated in FIG. 2, it may be desirable to provide a reference tie that may be secured around a portion of a spine during a surgical procedure and that may be trackable by a surgical navigation system. For example, it may be desirable to wrap a reference tie around bone or other anatomical structure. It may also be useful for a reference tie to be flexible or pliable, such that the reference tie may be positioned near an anatomical structure of interest. For example, if an orthopedic surgeon were interested in lumbar vertebrae, it may be useful to position reference ties around or near one or more lumbar vertebrae. In other examples, several reference ties may be used and each reference tie may include a unique identifying mark for distinguishing one reference tie from another reference tie.

Figure 3:
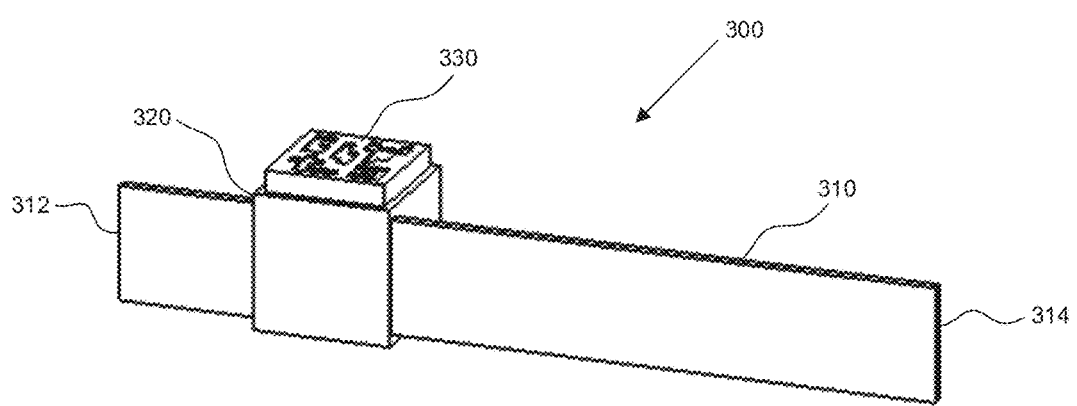
FIG. 3 is a reference tie, in accordance with an embodiment of the present application.

Reference is now made to FIG. 3, which is a reference tie 300, in accordance with an embodiment of the present application. The reference tie 300 in FIG. 3 may be secured around a portion of a spine during a surgical procedure and may be tracked by the surgical navigation system 110 (FIG. 1).

The reference tie 300 includes an elongate strap 310. The elongate strap 310 may include a first strap end 312 and a second strap end 314. As illustrated in FIG. 3, the reference tie 300 may have an open position. When the reference tie 300 is in an open position, the elongate strap 310 may be generally rectangular in shape. Although the elongate strap 310 is illustrated as having a generally rectangular shape, the elongate strap 310 may be modified to include any other shapes, such as tapered ends at the first strap end 312 or the second strap end 314. In other examples, the elongate strap 310 may include rounded corners or features at the first strap end 312 or the second strap end 314.

In some embodiments, the elongate strap 310 may be constructed of a flexible material. For example, the flexible material may allow the elongate strap 310 to be bent or maneuvered, such that a medical professional may wrap the elongate strap 310 around an anatomical structure. In some embodiments, pliability of the elongate strap 310 may be varied according to how the reference tie 300 is to be used. For example, if the reference tie 300 may be used near an anatomical structure that may be surrounded by ligaments and tissue, it may be desirable that the elongate strap 310 be easily pliable to allow a surgeon to maneuver the elongate strap 310 into a desired position. However, where the reference tie 300 may be secured to an anatomical feature that is easily accessible, the elongate strap 310 may be constructed of materials that are stiffer and that may retain a shape.

The reference tie 300 also includes a fastener 320 joined to the elongate strap 310 at the first strap end 312. The fastener 320 may be configured to secure the first strap end 312 to a portion of the second strap end 314. Although the fastener 320 illustrated in FIG. 3 is positioned at an edge of the first strap end 312, in some embodiments, the fastener 320 need not be positioned near the edge of the first strap end 312. For example, the fastener 320 may be positioned at a location near a median point of the elongate strap 310, or at any other location along the elongate strap 310 as desired.

The reference tie 300 may also include a fiducial marker 330 joined to at least one of the elongate strap 310 or the fastener 320. The fiducial marker 330 may be trackable by the surgical navigation system 110. In some embodiments, the reference tie 300 may include one or more fiducial markers. In FIG. 3, the fiducial marker 330 is illustrated as being affixed to the example fastener 320. In some embodiments, the fiducial marker 330 may be affixed to a portion of the elongate strap 310, such that components of the surgical navigation system 110 may detect the fiducial marker 330.

In some embodiments, the fiducial marker 330 may be coated with a hydrophobic material for preventing fluids from remaining on the surface of the fiducial marker 330. For example, the fiducial marker 330 may be constructed with hydrophobic material such that fluids are wicked away from the fiducial marker 330. Accordingly, the fiducial marker 330 may remain unobstructed such that the fiducial marker 330 may be detected by the surgical navigation system 110.

Figure 4:
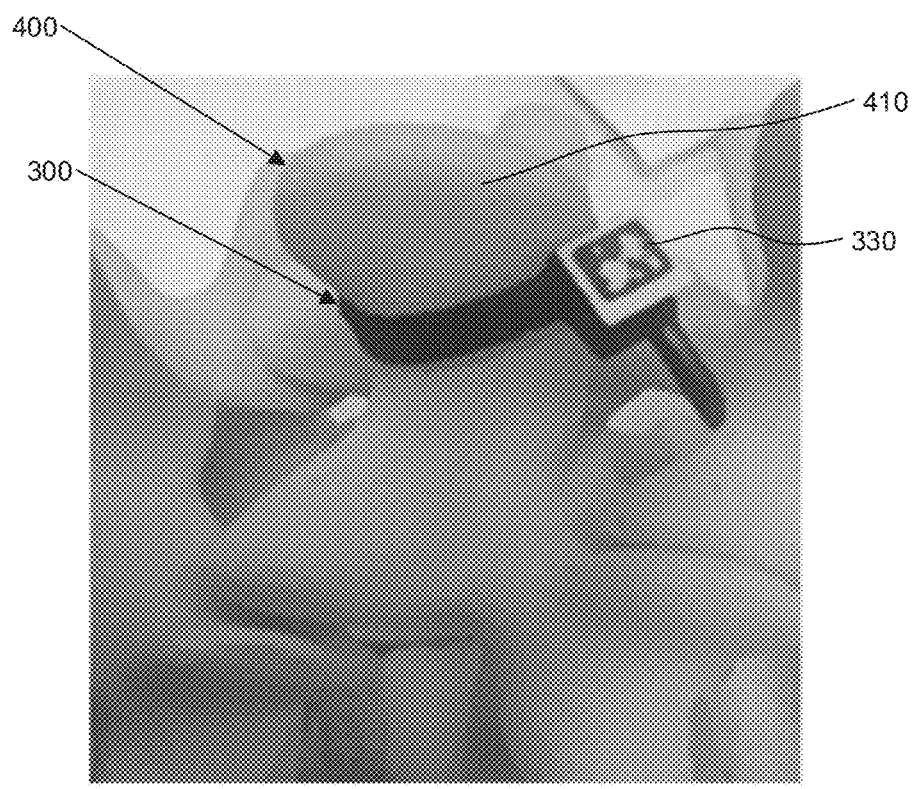
FIG. 4 is a side view of a reference tie secured around a portion of a spine, in accordance with an embodiment of the present application.

Reference is now made to FIG. 4, which is a side view of the example reference tie 300 (FIG. 3) secured around a portion of a spine. The spine may include a series of vertebrae, where each vertebra may be adjacent to another vertebra. A vertebra 400 may be made up of several components. For example, the vertebra 400 may be made up of components including an annulus, a pedicle, a transverse process, a superior and inferior articular process, and a spinous process. FIG. 4 generally illustrates the example reference tie 300 secured around a spinous process 410. The reference tie 300 may be secured around the spinous process 410 before or during a surgical procedure and may be tracked by the surgical navigation system 110 (FIG. 1). In FIG. 4, the reference tie 300 may be in a closed position (c.f. open position in FIG. 3).

The fiducial marker 330 may be a two-dimensional barcode. The two-dimensional barcode may be detectable and, subsequently, readable by the surgical navigation system 110. For example, the optical tracking camera 114 (FIG. 1) may include an image sensor for capturing an image of the two-dimensional barcode. Once an image of the two-dimensional barcode is captured, the surgical navigation system 110 may decode the information coded by the two-dimensional barcode. For example, the decoded information could include information for determining a three-dimensional position and/or orientation of the fiducial marker 330.

In some embodiments, the two-dimensional barcode of the fiducial marker 330 may be a unique code used for distinguishing the reference tie 300 from other reference ties present within the surgical space. By differentiating a reference tie from another reference tie, an anatomical structure having a reference tie secured thereon may be tracked by the surgical navigation system 110.

In some embodiments, the two-dimensional barcode may include information to be decoded by the surgical navigation system 110. For example, the two-dimensional barcode may be decoded by the surgical navigation system 110 to yield text strings. The text strings may include information regarding the patient, the surgical procedure, or any other required information. In some embodiments, the text strings may be associated with images captured by the optical tracking camera 114. However, it will be understood that in some embodiments, the two-dimensional barcode may simply be used for determining a three-dimensional position and orientation of the fiducial marker. Further, the two-dimensional barcode may also simply be used for distinguishing a given reference tie from another or an adjacent reference tie. That is, in some examples, the two-dimensional barcode may not need to yield text strings with readable information.

In some embodiments, the elongate strap 310 (FIG. 3) may be constructed from a flexible material. For example, the elongate strap 310 may be constructed from a flexible nylon composite that may be wrapped around a portion of a vertebra. As illustrated in FIG. 4, the elongate strap 310 may be wrapped around the circumference of the spinous process 410 and tightened to compress against the bone surface of the spinous process 410. Although the elongate strap 310 may be constructed from a flexible nylon composite, the elongate strap 310 can be constructed of other materials, such as plastic composites, or other similar materials. Further, the reference tie 300 may similarly be wrapped around any other structure of a vertebra. In some embodiments, the reference tie 300 need not be limited for use during a spinal procedure, but may be configured for use as a reference marker for other types of surgery such that reference ties may be fixed to other anatomical structures of a patient.

In some examples, the elongate strap 310 may be wrapped around the circumference of the spinous process 410 for a duration of a surgical procedure. Once the surgical procedure is complete, the reference tie 300 may be removed by cutting the elongate strap 310. As the elongate strap 310 may be cut upon completion of a surgical procedure, the reference tie 300 may be removed without requiring a surgeon to reverse steps taken to place the reference tie in position at the beginning of the surgical procedure. The reference tie 300 may be a disposable, single-use reference tie.

In some embodiments, the elongate strap 310 may be constructed from a flexible hydrophobic material. Thus, the reference tie 300 may be resistant to liquids and may be constructed to resist liquid absorption during the surgical procedure. Further, the flexible hydrophobic construction may be configured for preventing liquids or fluids from remaining on the surface of the elongate strap 310. The elongate strap 310 may be configured such that liquids are wicked away from the elongate strap 310 surface.

In some embodiments, the second strap end 314 of the reference tie 300 may include a rigid end tip configured for threading the elongate strap 310 through ligaments and for threading the elongate strap 310 around a portion of the spine, such as the spinous process 410. For example, the rigid end tip may be analogous to a sewing needle that may be used to guide sewing thread through fabric material.

In some embodiments, the elongate strap 310 may include two or more adjacent elongate portions configured to form a secured loop around a portion of the spine having varying circumference. For example, a spinous process may resemble a cylindrical solid; however, the circumference around the spinous process may be variable. Referring to the spinous process 410 illustrated in FIG. 4, the spinous process may have a larger circumference at a top portion as compared to a lower portion (e.g., "irregular sized surface"). To maximize a surface area interaction between the elongate strap and the bone surface of the spinous process 410, in some embodiments, the elongate strap may include two or more adjacent elongate portions that are parallel to another. Each of the adjacent elongate portions may be tightened around the spinous process by a different amount. The amount of tightening of the elongate portions may be dependent on the circumference of the spinous process at which the elongate portion comes into contact with.

In some embodiments, the reference tie 300 may be constructed using resorbable polymers. For example, the elongate strap 310, the fastener 320, and the fiducial marker 330 may be constructed from resorbable polymers. When the reference tie 300 is constructed from resorbable polymers, a surgeon may simply leave the reference tie 300 wrapped around a patient's anatomical feature (e.g., spinous process). Because the reference tie 300 may be constructed from resorbable polymers, the reference tie 300 may be resorbed by tissues and eliminate the need to explicitly remove the reference tie 300 upon completion of the surgical procedure.

Figure 5A:
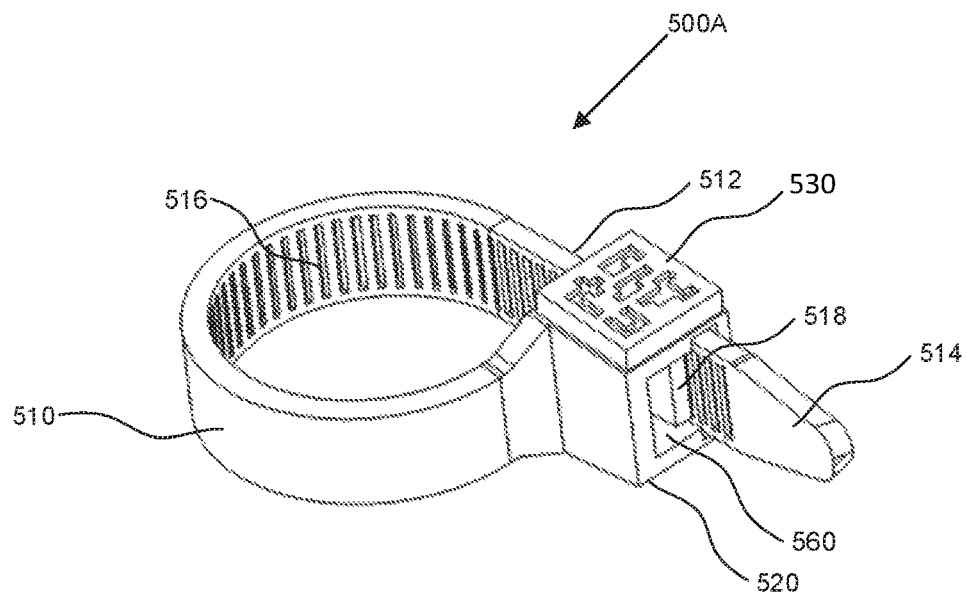
FIGS. 5A and 5B are perspective views of reference ties, in accordance with embodiments of the present application.
Figure 5B:
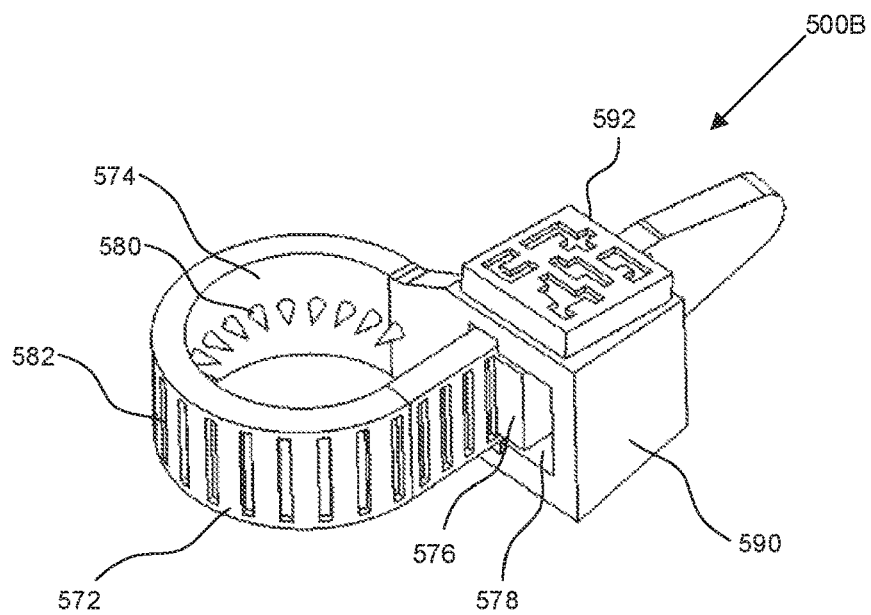

Reference is now made to FIGS. 5A and 5B, which are perspective views of reference ties, in accordance with embodiments of the present application. FIG. 5A illustrates a reference tie 500A including an elongate strap 510 having a first strap end 512 and a second strap end 514. The reference tie 500A also includes a fastener 520 joined to the elongate strap 510 at the first strap end 512. The elongate strap 510 is configured to form a secured loop. The reference tie 500A also includes a fiducial marker 530 joined to the fastener 520. In FIG. 5A, the fiducial marker 530 may include a surface of the fastener 520 and may be a barcode printed thereon. The fiducial marker 530 may be trackable by the surgical navigation system 110 (FIG. 5). The second strap end 514 may include a rigid end tip configured for threading the elongate strap 510 through ligaments.

In FIG. 5A, the elongate strap 510 may also include a series of ratchet teeth 516 along a portion of the elongate strap 510. In some embodiments, the series of ratchet teeth 516 may span the length of the elongate strap 510. In some embodiments, the series of ratchet teeth 516 may span a selected length of the elongate strap 510. The series of ratchet teeth 516 may be a series of raised structures for interfacing with the fastener 520.

The fastener 520 may include one or more pawls 518 to mate with the series of ratchet teeth 516 located along the portion of the elongate strap 510. The one or more pawls 518 may be configured within a strap receiving opening 560. The strap receiving opening 560 may receive the second strap end 514. The one or more pawls 518 may mate or engage with the series of ratchet teeth 516 as the elongate strap 510 is inserted and pulled through the strap receiving opening 560 and tightened around the patient's anatomical feature. When the series of ratchet teeth 516 engage with the one or more pawls 518 of the fastener 520, the elongate strap 510 may be configured as a secured loop and may not be loosened. To remove the reference tie 500A, a surgeon may cut the elongate strap 510.

In some embodiments, the fastener 520 may include a pawl release mechanism (not illustrated in FIG. 5A). When the pawl release mechanism is available, the pawl release mechanism may be configured to dis-engage the one or more pawls 518 from the series of ratchet teeth 516 and allow the reference tie 500A to be loosened from a surface of bone or from the patient's anatomical feature. For example, the pawl release mechanism may include a lever for disengaging the one or more pawls 518 in the series of ratchet teeth 516 that may be engaged with the one or more pawls 518.

Reference is now made to FIG. 5B, which illustrates another reference tie 500B, in accordance with an embodiment of the present application. The reference tie 500B may include an elongate strap 570 having an outer surface 572 and an anatomy facing surface 574. The reference tie 500B may include a fastener 590 joined to the elongate strap 570. The fastener 590 includes a strap receiving opening 578. The reference tie 500B may also include a fiducial marker 592 joined to the fastener 590. In FIG. 5B, the fiducial marker

592 may include a surface of the fastener 590 and may be a barcode or a set of reference marks printed thereon.

The anatomy facing surface 574 may be opposite the outer surface 572. For example, the anatomy facing surface 574 may be configured for contacting a bone surface when the elongate strap 570 is wrapped around and tightened to a portion of vertebra. The outer surface 572 may include a surface that does not contact a bone surface when the elongate strap 570 is wrapped around and tightened to the portion of the vertebra. In some embodiments, the anatomy facing surface 574 may also be configured to contact surfaces other than bone surfaces. For example, the reference tie 500B may be secured to anatomical features including ligaments or other types of tissues.

In some embodiments, the elongate strap 570 may include a series of protrusions 580. The series of protrusions 580 may be positioned on the anatomy facing surface 574 of the elongate strap 570. Each of the series of protrusions 580 may extend away from the elongate strap 570. In some embodiments, the series of protrusions 580 may extend in a direction perpendicular to the anatomy facing surface 574 of the elongate strap 570. In some embodiments, the series of protrusions may extend in a direction that may be at an angle less than 90 degrees from the anatomy facing surface 574 of the elongate strap 570.

In some embodiments, the series of protrusions may span the entire length of the anatomy facing surface 574 of the elongate strap 570. In some embodiments, the series of protrusions may span a selected length of the anatomy facing surface 574 of the elongate strap 570. The series of protrusions may resemble a series of small teeth and may be configured to increase a coefficient of friction between the anatomy facing surface 574 of the elongate strap 570 and a bone surface of the vertebra. For example, the series of protrusions 580 may be configured to improve fixation of the elongate strap 570 against bone surface. The series of protrusions 580 may be useful for improving fixation of the elongate strap 570 against bone that may have degenerated. In FIG. 5B, the series of protrusions 580 is illustrated as a single series of protrusions; however, the series of protrusions 580 on the anatomy facing surface 574 may be arranged in any other pattern.

The example reference tie 500B in FIG. 5B may also include a series of ratchet teeth 582. The series of ratchet teeth 582 may be positioned on the outer surface 572 of the elongate strap 570. The series of ratchet teeth 582 may be a series of raised structures for interfacing with the fastener 590.

The fastener 590 may include one or more pawls 576 within the strap receiving opening 578 of the fastener 590. The one or more pawls 576 may be configured to mate with the series of ratchet teeth 582 along the outer surface 572 of the elongate strap 570. That is, the one or more pawls 576 may mate with the series of ratchet teeth 582 as the elongate strap 570 may be pulled through the strap receiving opening 578 and tightened around the patient's anatomical feature.

In FIG. 5B, the one or more pawls 576 are oriented within the strap receiving opening 578 to mate with the series of ratchet teeth 582 on the outer surface 572 of the elongate strap 570. In contrast to the reference tie 500A in FIG. 5A, the one or more pawls 518 (FIG. 5A) are oriented within the strap receiving opening 560 (FIG. 5A) to mate with the series of ratchet teeth 516 (FIG. 5A) on an anatomy facing surface of the elongate strap 510.

In some embodiments, the series of ratchet teeth 516 may also provide the function of a series of protrusions along a portion of an anatomy facing surface of an elongate strap. For example, referring again to FIG. 5A, the series of ratchet teeth 516 for engaging the one or more pawls 518 may also function as protrusions for improving fixation of elongate strap 510 to bone. When a subset of the series of ratchet teeth 516 engage the one or more pawls 518, remaining ratchet teeth in the series of ratchet teeth 516 may be available to interface with bone or an anatomical feature. Overall, the reference tie 500A of FIG. 5A may include a series of ratchet teeth 516 for: (1) engaging with an anatomical feature surface when the reference tie 500A is secured around the anatomical feature; and (2) engaging with the one or more pawls 518 when the elongate strap 510 may be threaded through the strap receiving opening 560 of the fastener 520 and tightened around the anatomical feature.

In some embodiments, a fastener of a reference tie may be an adhesive fastener (not illustrated). The adhesive may be configured on an anatomy facing surface or an outer surface of an elongate strap. The adhesive may be protected with an adhesive liner until a surgeon is ready to configure the elongate strap in a secured loop around a portion of a spine. The surgeon may secure the reference tie by joining a portion of a first strap end to a portion of a second strap end using the adhesive. In some embodiments, the reference tie may be a pre-formed band and the band may be made of elastomer material. For example, the first strap end may be fastened to the second strap end using the adhesive. The surgeon may prepare the pre-formed bands prior to the surgical procedure. During the surgical procedure, the pre-formed bands may be stretched over exposed portions of the spine or other bone structure. The pre-formed bands may be held to the surface of the portions of the spine or other bone structure by elastic force or the tension from the elastomer material.

Figure 6:
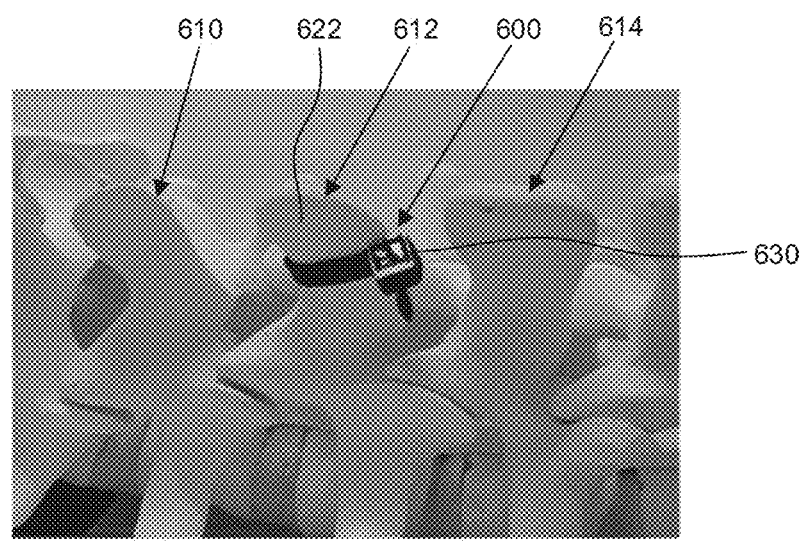
FIG. 6 is a side view of a series of vertebra of a spine and a reference tie secured around a portion of the spine, in accordance with an embodiment of the present application.

Reference is now made to FIG. 6, which is another side view of an example portion of a spine. In FIG. 6, a series of vertebra, identified generally by reference numerals 610, 612, and 614, is shown. In FIG. 6, a reference tie 600 is secured around an example spinous process 622. The reference tie 600 may include a fiducial marker 630 in the form of a two-dimensional bar code.

In some embodiments, the fiducial marker 630 may include a plurality of reference marks arranged in a unique geometric pattern (see e.g., FIG. 6). The plurality of reference marks may be detectable by the surgical navigation system 110 (FIG. 1). In response to detecting the plurality of reference marks, the surgical navigation system 110 may be configured to determine characteristics of the plurality of reference marks, including a position of the fiducial marker 630 in a surgical space, or the distance of the fiducial marker 630 from the optical tracking camera 114 (FIG. 1). For example, a position may refer to a set of coordinates that may be used to define a point in the surgical space or other coordinate space. The position may include coordinates for the point with 6 degrees of freedom, where the degrees of freedom may define an orientation, such as pitch, yaw, and roll rotational coordinates. In some examples, a combination of information relating to the position and the orientation may be referred to as a pose.

For example, several reference ties may be secured to objects prior to a surgical procedure. Reference ties may be secured around one or more anatomical features of a patient. As illustrated in FIG. 6, the reference tie 600 may be secured around the example spinous process 622. Prior to the surgical procedure, the surgical space may be translated to an optical coordinate space by way of an initial registration process. For example, registration may include touch point registration, in which a surgeon may utilize a pointer tool (not illustrated) to obtain touch point readings. The pointer tool may be tracked by the surgical navigation system 110 and the plurality of reference marks of the fiducial marker 630 may be located using the touch point readings obtained with the pointer tool. Using transforms, the plurality of reference marks may be translated to an optical coordinate space and a three-dimensional position of the fiducial marker 630 may be identified in the optical coordinate space. The three-dimensional position in the optical coordinate space may be defined by an x-axis, y-axis, and z-axis.

In another example, the surgical navigation system 110 may determine the distance of the fiducial marker 630 from the optical tracking camera 114. The optical tracking camera 114 may be a stereoscopic image capture device, and the optical tracking camera 114 may generate a three-dimensional image and determine the distance between the fiducial marker 630 and the optical tracking camera 114 or between the fiducial marker 630 and other fiducial markers in the surgical space.

Accordingly, if a reference tie were secured around each of the series of vertebra, identified generally by reference numerals 610, 612, 614, the surgical navigation system 110 may be configured to register or determine a three-dimensional position of each reference tie in a surgical space and, subsequently, track the three-dimensional position of each reference tie in the surgical space.

Figure 7:
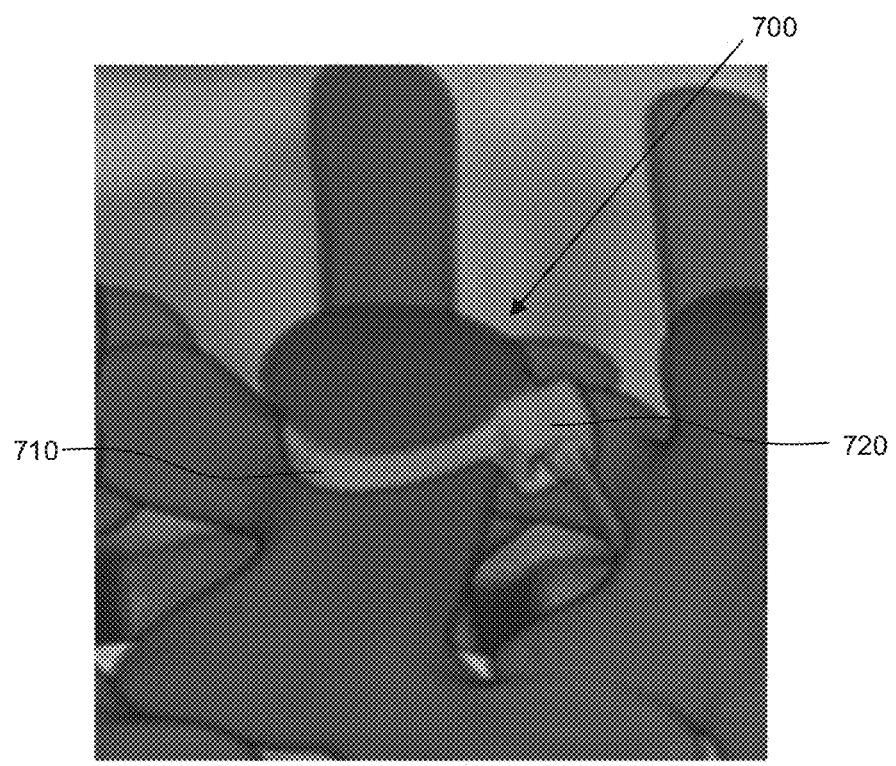
FIG. 7 is a perspective view of a reference tie secured around a portion of a spine in a three-dimensional image volume, in accordance with an embodiment of the present application.

Reference is now made to FIG. 7, which illustrates a reference tie 700 in an example three-dimensional image volume. In some embodiments, the three-dimensional image volume may be captured by imaging technology for producing magnetic resonance imaging (MRI), computerized tomography (CT), positron emission tomography (PET), or x-ray images. The reference tie 700 may include an elongate strap 710 having a first strap end and a second strap end. The reference tie 700 in FIG. 7 is illustrated in a closed position and the elongate strap 710 is joined to a fastener 720 to secure the elongate strap 710 around a spinous process.

To increase the viewability of the reference tie 700 in images produced using MRI, CT, PET, or x-ray imaging technology, the reference tie 700 may be coated with a contrast agent, such as a radiocontrast agent or an MRI contrast agent. As such, the position and orientation of the reference tie 700 may be distinguishable in the three-dimensional image produced using the MRI, CT, PET, or x-ray imaging technology. In some embodiments, the radiocontrast agent may be iodine or barium. The iodine or barium may be used to coat the elongate strap 710 or the fastener 720.

In some embodiments, contrast agents may be distinguishable in preoperative or intraoperative images. For example, a reference tie may include a fiducial marker joined to a fastener in the form of a barcode (not illustrated in FIG. 7). The barcode may be printed on the fastener using an ink mixed with a radiocontrast agent. Accordingly, the barcode printed with the radiocontrast agent may be viewable in images generated using the MRI, CT, PET, or x-ray imaging technology, as the case may be. Printing barcodes on the reference tie using, in part, a radiocontrast agent may increase readability of barcodes in images generated by MRI, CT, PET, or x-ray imaging technology. Because the barcodes may be identified in the three-dimensional image, the three-dimensional image may be mapped or merged, based in part on the barcode or other reference marks of the reference tie, with images captured by the surgical navigation system 110 during a surgical procedure. Overall, the contrast agent may be configured to be distinguishable in preoperative or intraoperative images from other portions of the preoperative or intraoperative images, respectively.

In some embodiments, reference ties may include fiducial markers produced using three-dimensional printing technology. The three-dimensional printing technology may utilize various materials for producing the fiducial marker. The choice of printing material may be determined based on material type that may yield high visual contrast when imaged using a particular imaging technology.

In some embodiments, a fiducial marker may include light reflecting portions. A fiducial marker may be configured to reflect light or other electromagnetic waves emitted by the optical tracking camera 114 (FIG. 1). For example, the fiducial marker may include light reflecting portions that reflect specific wavelengths of light incident on the fiducial marker, and the surgical navigation system 110 (FIG. 1) may be configured to detect the specific wavelengths of light and associate the reflected wavelength of light with the reference tie. In some embodiments, a reference tie 600 may be calibrated with a "white-light" image capture device prior to the surgical procedure. For example, prior to the surgical procedure, the surgical navigation system may emit "white-light" and the optical tracking camera 114 may detect reflected portions of the "white-light" from light reflecting portions of the fiducial marker. Because there may be some variation in light reflected by light reflecting portions, for example due to material variances due to manufacturing processes in the light reflecting portions, the light reflecting portions may be calibrated for detection prior to the surgical procedure. By detecting the reflected portions of the "white-light" prior to the surgical procedure, the surgical navigation system 110 may be calibrated to recognize the specific light reflecting fiducial markers during the surgical procedure.

In some embodiments, the fiducial marker may be configured to include a combination of features including the two-dimensional barcode, radiocontrast agent, light reflecting portions, or any other features detectable by the surgical navigation system 110 for identifying the reference tie 600.

Figure 8:
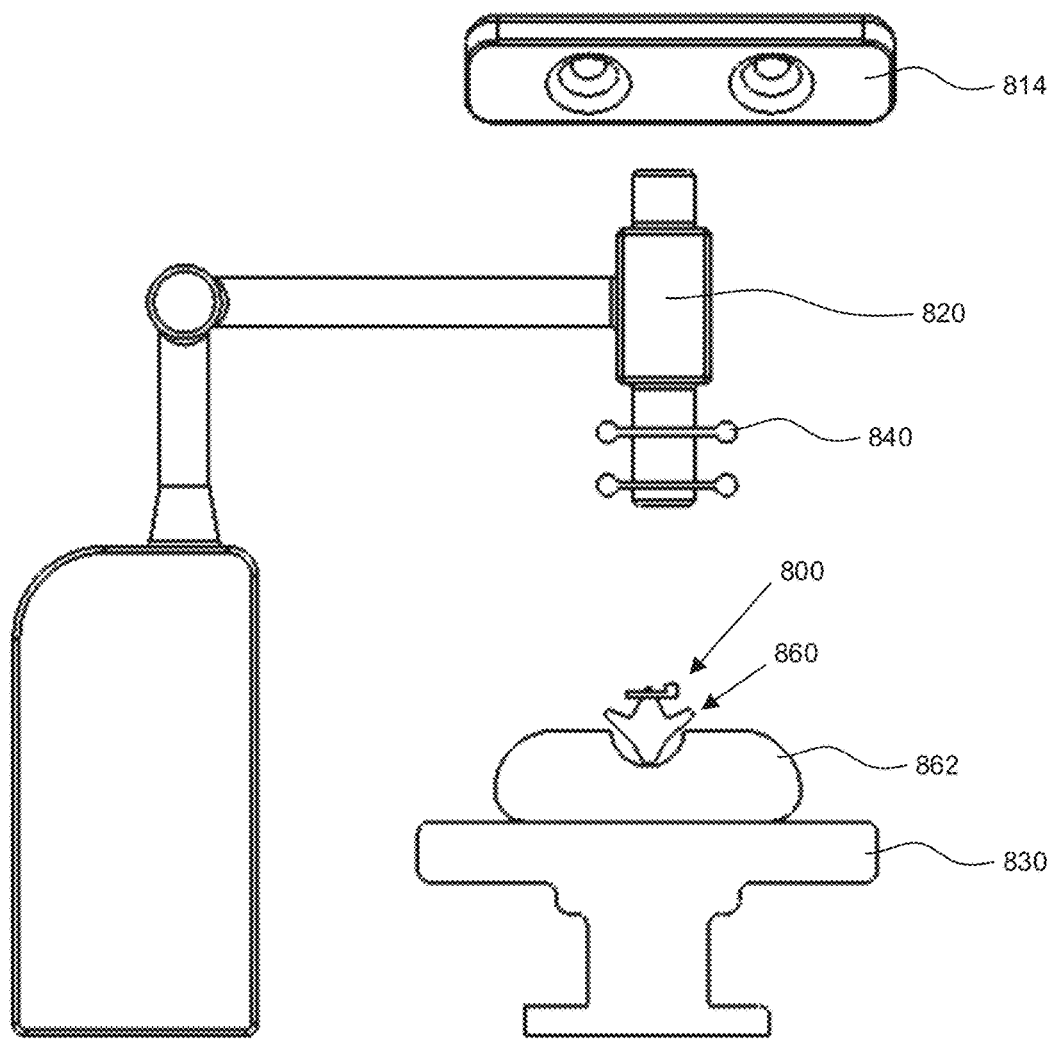
FIG. 8 is a front view of a surgical system illustrating a reference tie secured to a portion of a vertebra on a patient, in accordance with an embodiment of the present application.

Reference is now made to FIG. 8, which is a front view of an exemplary surgical system illustrating a reference tie 800 secured to a portion of vertebra 860 of a patient 862. In FIG. 8, an optical tracking camera 814, a scope instrument 820, a surgical platform 830, and a fiducial array 840 affixed to the scope instrument 820 are illustrated. Other components may be included in the surgical system of FIG. 8 but may not be illustrated for ease of exposition. The optical tracking camera 814, the scope instrument 820, the surgical platform 830, and the fiducial array 840 may be similar to the optical tracking camera 114, scope instrument 120, surgical platform 130, and reference tie 140 described with reference to FIG. 1.

In some embodiments, the reference tie 800 may be secured to a portion of the spine, such as to a vertebra. For example, the reference tie 800 may be secured around a spinous process of a vertebra. The reference tie 800 may include an elongate strap with a first strap end and a second strap end. The reference tie 800 may also include a fastener for securing the first strap end to a portion of the second strap end. The reference tie 800 may also include a fiducial marker trackable by the optical tracking camera 814 of the surgical navigation system. The elongate strap may be looped around the spinous process and a portion of the second strap end may be affixed to the first strap end using the fastener. The portion of the second strap end to be affixed to the first strap end using the fastener may be determined by a surgeon. For example, the reference tie 800 may be tightened around a spinous process such that an anatomy facing surface of an elongate strap of the reference tie 800 sits flush against a bone surface (e.g., spinous process). Although the foregoing example describes securing the reference tie 800 around a spinous process, the reference tie 800 may also be secured around any other portion of the vertebra or the spine. For example, the reference tie 800 may also be secured around a transverse process or around the body of the vertebra.

Although one reference tie 800 is illustrated in FIG. 8, in some embodiments, a plurality of reference ties may be secured along the spine. A surgeon may be performing a spinal procedure on a lumbar region of a patient's spinal column. The surgeon may desire a reference point marker at each of the lumbar vertebra. Accordingly, a unique reference tie may be secured to each of the lumbar vertebra (e.g., L1, L2, L3, L4, L5). Although reference ties may be secured to lumbar vertebra, in some examples, the reference ties could also be secured to the thoracic and cervical regions of the spine. Each of the reference ties may include a fiducial marker that is distinguishable from another fiducial marker of an adjacent reference tie. For example, the reference tie secured to the L1 vertebra may include a two-dimensional barcode (e.g., fiducial marker) that may be coded with information for identifying that reference tie. An adjacent reference tie secured to the L2 vertebra may include a two-dimensional barcode (e.g., fiducial marker) that may be coded with information to distinguish this adjacent reference tie from the reference tie secured to the L1 vertebra. Accordingly, when the array of reference ties are within a field of view of the optical tracking camera 814, the surgical navigation system may distinguish a given reference tie from adjacent reference ties. Accordingly, each of the reference ties in the array of reference ties may be a proxy for identifying vertebra or for distinguishing a given vertebra from other vertebra. Further, by securing an array of reference ties to multiple locations along a spine, the surgical navigation system may be configured to track surgical instruments having fiducial markers attached thereon relative to the array of reference ties.

In some embodiments, when multiple reference ties are secured to objects, the surgical navigation system may track objects with greater granularity or precision compared to when fewer reference ties may be used. Generally, a greater number of reference points (or "landmarks") enables object tracking with greater precision.

In the example scenario illustrated in FIG. 8, the scope instrument 820 being tracked may be mounted on a movable arm. The scope instrument 820 may include the fiducial array 840 affixed thereon. The fiducial array 840 may be a plurality of reference markers detectable by the optical tracking camera 814. The plurality of reference markers may also be arranged in a unique geometric pattern. Accordingly, the geometric pattern may be recognizable by the surgical navigation system 110, and the surgical navigation system 110 may determine a position of the fiducial array 840 by identifying the location of the fiducial array in an optical coordinate space.

Figure 9:
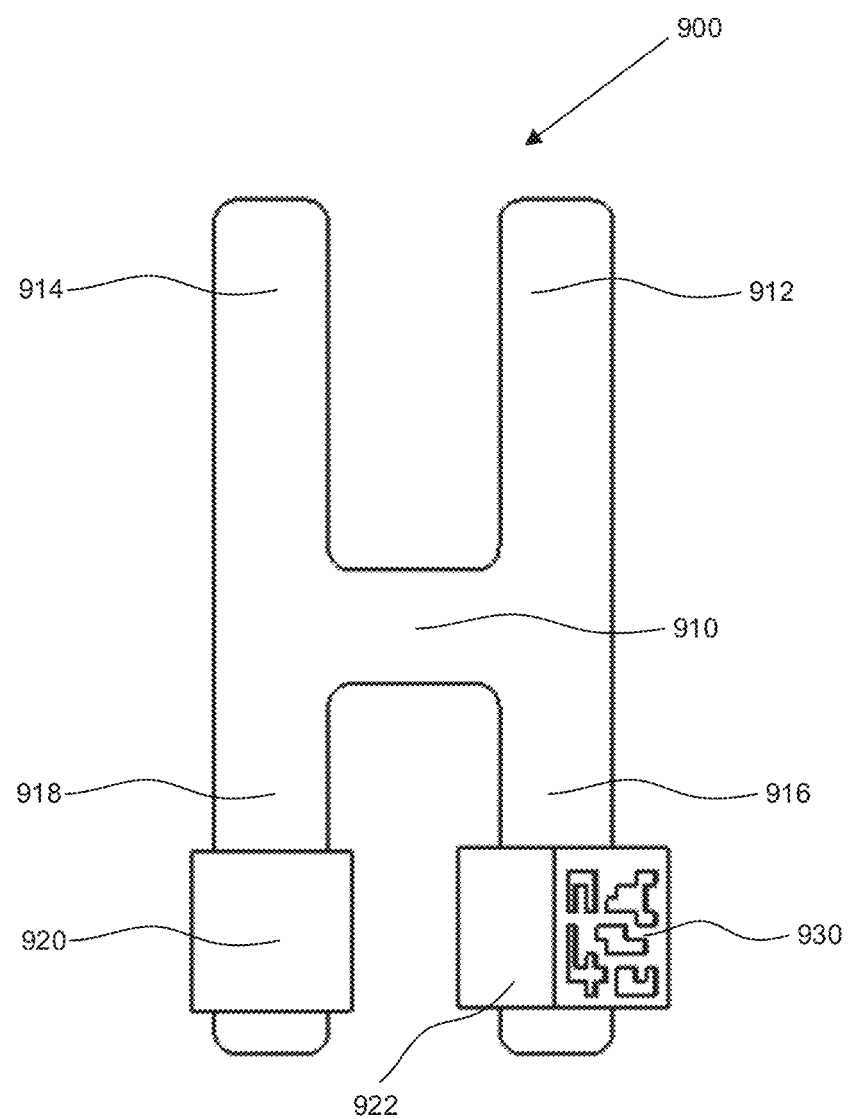
FIG. 9 is a reference tie with a plurality of attachment portions, in accordance with an embodiment of the present application.

Reference is now made to FIG. 9, which is a reference tie 900, in accordance with an embodiment of the present application. The reference tie 900 may be secured to a portion of a spine during a surgical procedure and may be tracked by the surgical navigation system 110 of FIG. 1. The reference tie 900 may include an attachment body 910 having a plurality of attachment portions. The plurality of attachment portions may include a first attachment portion 912, a second attachment portion 914, a third attachment portion 916, and a fourth attachment portion 918. Although four attachment portions are illustrated in FIG. 9, in some embodiments, the attachment body 910 may include any number of attachment portions.

Before beginning a surgical procedure, a surgeon may secure the reference tie 900 to the portion of the spine. In doing so, the surgeon may utilize as many of the attachment portions as required. For example, the surgeon may utilize all the attachment portions for securely affixing the reference tie 900 to the spine. In another example, the surgeon may utilize a select number of attachment portions (e.g., utilize the first attachment portion 912 and the third attachment portion 916) and separate the unused attachment portions (e.g., the second attachment portion 914 and the fourth attachment portion 918) from the attachment body 910.

The reference tie 900 may also include at least one fastener joined to at least one of the plurality of attachment portions. The at least one fastener is for securing one of the plurality of attachment portions to another of the plurality of attachment portions for securing the attachment body 910 around the portion of the spine. For example, the reference tie 900 illustrated in FIG. 9 includes a first fastener 920 joined to the fourth attachment portion 918 and a second fastener 922 joined to the third attachment portion 916. For example, the first fastener 920 may be configured to secure an end portion of the fourth attachment portion 918 to an end portion of the second attachment portion 914. Similarly, the second fastener 922 may be configured to secure an end portion of the third attachment portion 916 to an end portion of the first attachment portion 912.

The reference tie 900 of FIG. 9 may also include a fiducial marker 930 joined to the second fastener 922, where the fiducial marker 930 may be trackable by the surgical navigation system 110.

Generally, as apparent from the present application, reference ties may be used as "landmarks". Accordingly, in some embodiments, preoperative images using various imaging technologies may be overlaid for providing a consolidated image or images. For example, an MRI image of a patient's vertebra having a reference tie secured thereon may be merged with an x-ray image of the patient's vertebra having the same reference tie secured thereon. Accordingly, the merged preoperative image may collaboratively illustrate image details detectable by each respective imaging technology.

In some embodiments, the embodiments of reference ties described in the present disclosure may be used together with the attachment clamp 230 (FIG. 2) illustrated in FIG. 2 to improve the fixation of the attachment clamp 230 to areas of compromised bone. The embodiments of the reference ties illustrated in FIGS. 3, 4, 5A, 5B, 6, and 7 may, for example, be configured to improve the stability of the attachment clamp 230 when the attachment clamp 230 is used to couple the marker frame 212 (FIG. 2) to a patient.

Certain adaptations and modifications of the described embodiments can be made. Therefore, the above discussed embodiments are considered to be illustrative and not restrictive.

What is claimed is:

1. A reference tie to be secured around a portion of a spine during a surgical procedure and to be tracked by a surgical navigation system, the reference tie comprising:

an elongate strap having a first strap end and a second strap end;

a fastener joined to the elongate strap at the first strap end, the fastener for securing the first strap end to a portion of the second strap end, wherein the elongate strap is configured to form a secured loop around the portion of the spine; and a fiducial marker joined to at least one of the elongate strap or the fastener, wherein the fiducial marker includes a plurality of reference marks arranged in a unique geometric pattern, and wherein the unique geometric pattern is detectable by the surgical navigation system for determining at least one of a position or an orientation of the fiducial marker in three-dimensional space.

2. The reference tie of claim 1, wherein the fiducial marker is coated in a hydrophobic material.

3. The reference tie of claim 1, wherein the elongate strap or the fastener is coated with a contrast agent.

4. The reference tie of claim 3, wherein the contrast agent includes a radiocontrast agent or an MRI contrast agent.

5. The reference tie of claim 1, wherein the fiducial marker includes a two-dimensional barcode readable by the surgical navigation system.

6. The reference tie of claim 5, wherein the two-dimensional barcode is printed on the fiducial marker with ink including a contrast agent, the contrast agent configured to be distinguishable in an image from other portions in the image, wherein the image includes at least one of a preoperative image or an intraoperative image.

7. The reference tie of claim 1, wherein the elongate strap further comprises a series of ratchet teeth along a portion of the elongate strap, and wherein the fastener further comprises:
  a strap receiving opening for receiving the second strap end; and
  a pawl positioned within the strap receiving opening to engage the series of ratchet teeth when the second strap end is inserted into the strap receiving opening.

8. The reference tie of claim 7, wherein the elongate strap includes an outer surface and an anatomy facing surface opposing the outer surface, the reference tie further comprising:
  a series of protrusions along a portion of the anatomy facing surface of the elongate strap for increasing a coefficient of friction between the anatomy facing surface and a bone surface of a vertebrae.

9. The reference tie of claim 8, wherein the series of ratchet teeth is the series of protrusions along the portion of the anatomy facing surface of the elongate strap.

10. The reference tie of claim 1, wherein the elongate strap comprises a flexible hydrophobic material.

11. The reference tie of claim 9, wherein the second strap end includes a rigid end tip configured for threading the elongate strap through ligaments around the portion of the spine.

12. The reference tie of claim 1, wherein the fastener includes an adhesive for securing the first strap end to a portion of the second strap end.

13. The reference tie of claim 1, wherein the elongate strap includes two or more adjacent elongate portions configured to form a secured loop around the portion of the spine having varying circumference.

14. The reference tie of claim 1, wherein the elongate strap, the fastener, and the fiducial marker are constructed from resorbable polymers configured to be resorbed by tissue.

15. The reference tie of claim 1, wherein the fiducial marker includes a light reflecting portion trackable by the surgical navigation system.

16. The reference tie of claim 1, wherein the elongate strap is constructed of elastomer material, and wherein the first strap end and the second strap end are joined by an adhesive, whereby the reference tie fits over the portion of the spine and is fastened to the portion of the spine by elastic force.

17. A reference tie to be secured to a portion of a spine during a surgical procedure and to be tracked by a surgical navigation system, the reference tie comprising:
  an attachment body having a plurality of attachment portions;
  at least one fastener joined to at least one of the plurality of attachment portions, the at least one fastener for securing one of the plurality of attachment portions to another of the plurality of attachment portions, wherein the attachment body is configured to be secured around the portion of the spine; and
  a fiducial marker joined to at least one of the attachment body, the plurality of attachment portions, or the at least one fastener, wherein the fiducial marker includes a plurality of reference marks arranged in a unique geometric pattern, and wherein the unique geometric pattern is detectable by the surgical navigation system for determining at least one of a position or an orientation of the fiducial marker in three-dimensional space.

18. The reference tie of claim 17, wherein at least one of the plurality of attachment portions include a rigid end tip configured for threading at least one of the attachment portions through ligaments around a portion of the spine.

* * * * *